Figure 1:
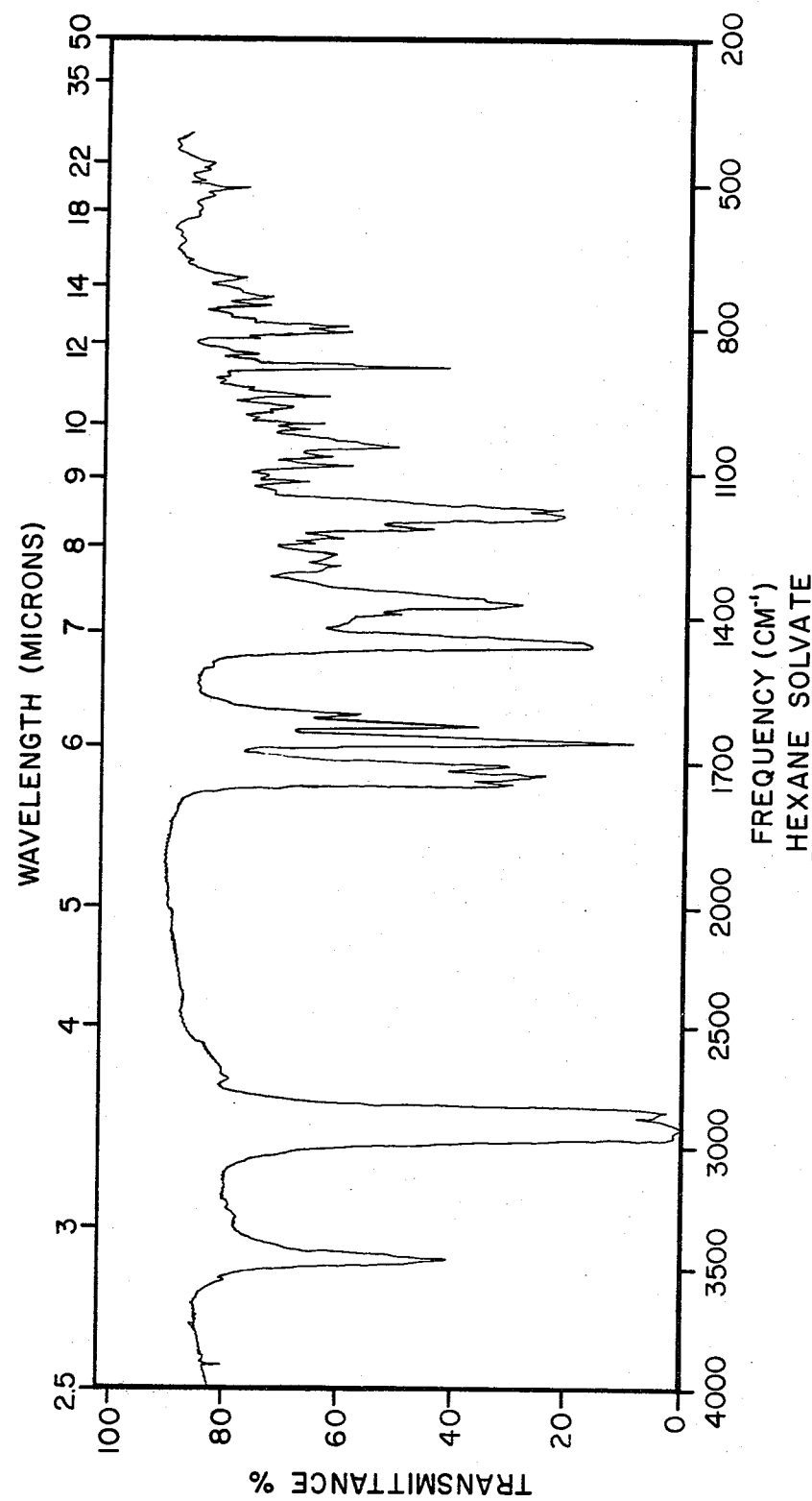

United States Patent [19]

Finckenor

[11] 4,225,597

[45] Sep. 30, 1980

[54] BECLOMETHASONE DIPROPIONATE-HEXANE SOLVATE AND AEROSOLS PREPARED THEREFROM

[75] Inventor: Lawrence E. Finckenor, Wayne, N.J.

[73] Assignee: Schering Corporation, Kenilworth, N.J.

[21] Appl. No.: 728,570

[22] Filed: Oct. 1, 1976

[51] Int. Cl.² ............................................. A61K 31/56
[52] U.S. Cl. ........................................................ 424/243
[58] Field of Search ........................................ 424/243

[56] References Cited

U.S. PATENT DOCUMENTS

| 3,845,085 | 10/1974 | Phillipps et al. | 260/397.45 |
| 4,044,126 | 8/1977 | Cook et al. | 424/243 |

Primary Examiner—Elbert L. Roberts

[57] ABSTRACT

A beclomethasone dipropionate-hexane solvate, useful in the preparation of beclomethasone dipropionate aerosols is disclosed herein. The new n-hexane solvate is stable when stored as bulk, and convenient and cheap to prepare. The trichlorofluoromethane solvate prepared by contacting micronized n-hexane solvate with trichlorofluoromethane affords beclomethasone dipropionate-trichlorofluoromethane solvate which retains its small particle size.

5 Claims, 1 Drawing Figure

HEXANE SOLVATE

BECLOMETHASONE DIPROPIONATE-HEXANE SOLVATE AND AEROSOLS PREPARED THEREFROM

This invention relates to a novel solvate of beclomethasone dipropionate and a method of using it to prepare aerosol formulations of beclomethasone dipropionate. More particularly, this invention is concerned with the n-hexane solvate of beclomethasone dipropionate having 94–96% by weight beclomethasone diprionate solvated with 4–5% by weight n-hexane. Chemically, beclomethasone dipropionate is known as 9α-chloro-16β-methyl-$\Delta^{1,4}$-pregnadiene-11β,17α,21-triol-3,20-dione 17α,21-dipropionate and is represented by the following structural formula:

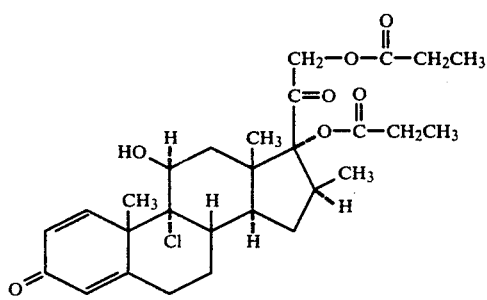

For the purposes of this invention, we define the term "solvate" as a crystalline material in which the steroid and the solvating species are associated. The ratio of the steroid to the solvating species is approximately stoichiometric; that is, approximately 1 mole of n-hexane is associated with 3–4 moles of the steroid. No mechanism of association is implied, but the solvating species may possibly occupy "holes" in the crystal lattice of the steroid. The solvating species is also referred to herein as a "solvent," this word being used in its general sense of a liquid which may dissolve or be associated with the steroid.

Beclomethasone dipropionate in an aerosol form is a useful steroid for the treatment of chronic allergic asthma (Brit. Med. J., 1, 585–590 (1972)). This drug is typically administered in an aerosol unit containing a microcrystalline suspension of beclomethasone dipropionate in propellants (usually trichlorofluoromethane). The drug must be micronized prior to use in an aerosol formulation in order to obtain particles of effective dosage size. However, when unsolvated drug is introduced into the aerosol formulation solvation of the drug occurs and the resultant crystal growth reduces the amount of suitable particle size available in the spray and also causes clogging of the aerosol spray valves. To overcome this problem of crystal growth, it has previously been found useful to prepare a solvate of the drug with the trichlorofluoromethane propellant prior to micronization of the drug (British Pat. No. 1,429,184). The drug solvate is then micronized and mixed with the remaining aerosol propellants. The beclomethasone dipropionate-trichlorofluoromethane solvate thus enables one to prepare a suitable aerosol form but provides other manufacturing difficulties in that the solvate is not stable with respect to solvent when stored as bulk. Trichlorofluoromethane is released when the solvate is stored at room temperature or above and thus the solvate must be used rather promptly or stored at a refrigerated temperature. Storage at refrigerated temperatures is both expensive and inconvenient, particularly when the bulk drug solvate is to be shipped. A substantial portion (up to ½) of the trichlorofluoromethane solvent is lost from the trichlorofluoromethane solvate during the micronization. The loss of the trichlorofluoromethane solvent from the drug solvate results in a loss of the drug in the aerosol formulation since any unsolvated drug will tend to crystallize and thus not be available in the aerosol spray. The lost trichlorofluoromethane solvent is also a potential environmental hazard.

It has been surprisingly found that beclomethasone dipropionate forms a solvate with n-hexane which is stable with respect to solvent when stored as bulk. The infrared absorption spectra of the n-hexane-beclomethasone dipropionate solvate of this invention is shown in FIG. I. The beclomethasone dipropionate-n-hexane solvate contains 4–5% by weight n-hexane and 94–96% by weight beclomethasone dipropionate and thus contains approximately 1 mole of hexane for every 3–4 moles of beclomethasone dipropionate. This beclomethasone dipropionate-n-hexane solvate is stable with respect to the solvent at temperatures up to about 100°. (Solvent begins to be lost at about 105° C.) Additionally, when micronized n-hexane solvate is used to prepare the trichlorofluoromethane solvate, the particle size of the beclomethasone dipropionate trichlorofluoromethane solvate remains in the micronized size range of 1–10μ.

The beclomethasone dipropionate-n-hexane solvate is prepared by dissolving the beclomethasone dipropionate in a suitable organic solvent, such as methylene chloride or acetone, and then adding n-hexane to this solution resulting in the formation of a precipitate. The precipitate is filtered and dried to afford the beclomethasone dipropionate-n-hexane solvate.

The n-hexane solvate of beclomethasone dipropionate is simpler to prepare than the trichlorofluoromethane in that it does not require the large volumes of solvent to prepare as is the case with the freon solvate.

Moreover, when the beclomethasone dipropionate-n-hexane solvate is contacted with a relatively small volume of trichlorofluoromethane, for instance, 15 liters per kg of solvated steroid, the n-hexane of solvation is apparently exchanged for fluorotrichloromethane resulting in formation of the beclomethasone dipropionate-trichlorofluoromethane solvate. (Preparation of the fluorotrichloromethane solvate not using this method would require about 140 liters per kg of steroid.) This procedure may be followed and the beclomethasone dipropionate-trichlorofluoromethane solvate isolated. Alternatively and preferably, micronized beclomethasone dipropionate-n-hexane solvate may be placed directly in the aerosol cannister with the trichlorofluoromethane propellants to afford an aerosol formulation which does not exhibit crystal growth and which provides beclomethasone dipropionate in a particle size suitable for systemic absorption.

The beclomethasone dipropionate-n-hexane solvate may be micronized after formation and then utilized directly in an aerosol formulation. Alternatively, after micronization, it may be slurried with trichlorofluoromethane to afford the beclomethasone dipropionate-trichlorofluoromethane solvate. The beclomethasone dipropionate-trichlorofluoromethane solvate prepared by this method retains the particle size of the micronized beclomethasone dipropionate-hexane solvate and thus may be used directly without further micronization in an aerosol formulation.

The amount of n-hexane present in the solvate of this invention is considered biologically insignificant and thus the n-hexane solvate may be used directly in a formulation without toxicological affects.

The aerosol propellants and valves suitable for use in this invention are standard and well known in the art. A particularly suitable inhaler system is that presently marketed as the Vanceril ® inhaler.

The following examples describe in detail the compositions of the present invention. It will be apparent to those skilled in the art that many modifications, both of materials and methods, may be practiced without departing from the purpose and intent of this disclosure.

EXAMPLE 1

Beclomethasone Dipropionate-n-Hexane Solvate

Dissolve 300 g of beclomethasone dipropionate in 2 liters of methylene chloride at reflux. Treat with 15 g activated charcoal for 15 minutes at reflux and filter while hot. Concentrate the filtered solution to a volume of 900 ml and while maintaining reflux add slowly 900 ml of n-hexane. Cool to 0–10° C. Filter the resultant precipitate and wash with n-hexane. Dry the precipitate in air at <50° C. until constant weight to afford beclomethasone dipropionate-n-hexane solvate having an $[\alpha]/D^{25} = +85.5 \pm 2°$ in dioxane and an $\epsilon 1\%$ (extinction coefficient) in 1% solution=275±10 at 239 mu. Analysis by gas chromatography shows an n-hexane content of 4.6%. The beclomethasone dipropionate content (determined by ultraviolet assay) is 94.5%.

EXAMPLE 2

Beclomethasone Dipropionate-n-Hexane Solvate

Dissolve 100 g of dipropionate in 1.5 liters of acetone at reflux. Treat with 5 g of activated charcoal for 15 minutes and filter while hot. Concentrate the filtered solution to 0.5 liter. While maintaining reflux, slowly add 0.5 liter of n-hexane. Cool to 0–10° C. Filter the precipitate and wash with cold n-hexane. Dry the precipitate in air at 50° C. until constant weight to yield beclomethasone dipropionate-n-hexane solvate. The beclomethasone dipropionate content (determined by ultraviolet assay) is 94.6%.

EXAMPLE 3

| Reclomethasone Inhaler | |
|---|---|
| Formula | mg/container (200 doses) |
| Beclomethasone Dipropionate* (micronized) | 10.0 |
| Oleic Acid | 1.0 |
| Fluorotrichloromethane | 4,739.0 |
| Dichlorodifluoromethane | 12,250.0 |
| to make | 17,000.0 |

*Charged as beclomethasone dipropionate-hexane solvate equivalent to 10 mg of beclomethasone dipropionate.

Procedure

Add oleic acid to previously cooled fluorotrichloromethane and mix with a high sheer mixer. While mixing, add the required amount of beclomethasone dipropionate-hexane solvate and continue mixing until homogeneous. If necessary, adjust the suspension to the required weight with fluorotrichloromethane. Meter required amount of suspension into each can. Crimp the valves onto the can. Pressure fill through valve required amount of dichlorodifluoromethane.

What is claimed is:

1. A solid composition of matter which consists of a beclomethasone dipropionate-n-hexane solvate characterized by an infrared absorption spectra substantially as shown in FIG. 1 and comprising 94–96% by weight beclomethasone dipropionate and 4–5% by weight n-hexane.

2. A method of preparing micronized beclomethasone dipropionate-fluorotrichloromethane solvate which comprises contacting micronized beclomethasone dipropionate-n-hexane solvate of claim 1 with trichlorofluoromethane.

3. A method according to claim 2 wherein the micronized beclomethasone dipropionate-n-hexane solvate is slurried with the trichlorofluoromethane.

4. In a method for preparing a beclomethasone dipropionate-fluorotrichloromethane solvate in an aerosol formulation, the improvement which comprises contacting beclomethasone dipropionate-n-hexane solvate with trichlorofluoromethane in situ.

5. In a method for preparing an aerosol formulation of beclomethasone dipropionate in a suitable aerosol propellant suitable for inhalation therapy, the improvement which comprises utilizing beclomethasone dipropionate-n-hexane solvate.

* * * * *